United States Patent [19]
Dure-Smith et al.

[11] 3,937,800
[45] Feb. 10, 1976

[54] BRONCHOGRAPHIC X-RAY CONTRAST METHOD

[76] Inventors: Peter Dure-Smith; Roger L. Schnaare, both of 1500 Spring Garden St., Philadelphia, Pa. 19101

[22] Filed: Apr. 3, 1974

[21] Appl. No.: 457,462

Related U.S. Application Data

[63] Continuation-in-part of Ser. No. 272,632, July 17, 1972, abandoned.

[52] U.S. Cl. .................................................. 424/4
[51] Int. Cl.² ............................................ A61K 29/02
[58] Field of Search ........................................ 424/4

[56] References Cited
UNITED STATES PATENTS

| | | | |
|---|---|---|---|
| 1,918,884 | 7/1933 | Zellmann et al. | 424/4 |
| 2,387,704 | 10/1945 | McLachlan, Jr. | 424/4 X |

FOREIGN PATENTS OR APPLICATIONS

| | | | |
|---|---|---|---|
| 1,132,576 | 11/1968 | United Kingdom | 424/4 |

OTHER PUBLICATIONS

Nadel et al., Investigative Radiology, July–Aug. 1968, Vol. 3, pp. 229 to 238.
Chem. Abs., 1942, Vol. 38, p. 6191.
Chem. Abs., 1953, p. 12026.
Chem. Abs., 1952, Vol. 48, p. 5589.
Chem. Abs., 1958, Vol. 46, p. 5959.

*Primary Examiner*—Dale R. Ore
*Attorney, Agent, or Firm*—Joseph A. Marlino

[57] ABSTRACT

An X-ray contrast method containing as the essential radioopaque ingredient finely divided tantalum metal dispersed in a liquid vehicle having critical viscosity and flow properties. The metal has an average particle diameter in the range from about 0.5 to about 30 microns, and preferably in the range from about 1 to about 5 microns in a physiologically and pharmaceutically acceptable amount for use in obtaining X-ray films of sufficient clarity and detail for use in bronchography.

1 Claim, No Drawings

BRONCHOGRAPHIC X-RAY CONTRAST METHOD

This application is a continuation-in-part of copending Ser. No. 272,632, filed July 17, 1972, now abandoned.

The present invention relates to compositions to be introduced into the lungs, to serve as bronchographic contrast media and especially to oily suspensions but not limited to suspensions of an oily nature containing as the essential X-ray opaque ingredient finely divided tantalum metal.

The essential object of bronchographic contrast media is to provide a coating on various parts of the bronchial tree of the lung, the coating being opaque to X-rays. Such a coating allows an X-ray film of the coated parts of the bronchial tree to be produced in which such parts of the bronchial tree can be visualized in considerable detail and clarity. It is generally recognized that a contrast medium, to be effective, must contain an X-ray opaque (radioopaque) agent. This agent should have certain characteristics, the prime three being the ability to block the passage of X-rays (radioopacity), the ability to stick or cling to the mucosa lining the bronchial walls and safety for use in the lung. The ability to block the passage of X-rays (radioopacity) depends on the atomic number, i.e., the position in the periodic table of the elements. The ability to stick to the mucosa lining the bronchial walls is related to the condition of said tissue, the various surface characteristics of the X-ray opaque agent and the properties of the suspending vehicle. Safety requires that these be such that the X-ray opaque agent coat the mucosa lining the bronchial tree without causing excessive irritation to normal or diseased bronchial tissue and that the contrast medium be eliminated from the bronchial tree in a clinically safe and convenient manner. Other important parameters to be considered in choosing X-ray opaque agents for bronchographic contrast media are compatibility with common contrast media ingredients, such as suspending agents, viscosity builders, surfactants and dispersing agents, etc. and compatability with therapeutic agents which might be incorporated into the contrast medium, such as antibiotics, anesthetics, etc. A still further requirement is that the contrast medium be of acceptable thickness or viscosity; the medium should flow readily into the bronchi and bronchiols of the lung without allowing significant flow into the pulmonary paranchyma.

Heretofore, the literature has disclosed the use of iodine containing compounds as X-ray opaque agents in various compositions (see e.g., U.S. Pat. No. 3,021,260; U.S. Pat. No. 3,033,757, and U.S. Pat. No. 3,047,466). Among such iodine containing compounds, the iodized vegetable oils, e.g., iodized poppyseed oil, tend to have the iodine more or less strongly bound to the oil and furthermore some of the iodine may be in the free form. The presence of iodine, whether strongly bound or not, may be dangerous when used in patients who are sensitive to iodine. In other iodine containing compounds, e.g., propyliodone marketed under the trademark "Dionosil," the iodine is chemically bound, hence less toxic than free iodine. However, iodine, whether free, strongly bound or chemically bound acts as a local irritant and causes inflammation of the bronchi and bronchiols of the human lung. Even in non-sensitive patients, such iodine containing agents may produce iodism.

The usual and acceptable mechanism for elimination of a bronchographic contrast media from the lungs is postural drainage and normal expectoration. In addition, iodine containing agents are often hydrolyzed in the lungs and the liberated iodine excreted by the kidneys thus increasing the chance of toxicity. It has been suggested that the addition of a material, e.g., sulfanilamide, to the contrast medium composition may hasten removal of the iodine containing agent. This only adds to the possibility of toxicity.

Unlike conventional iodine containing X-ray opaque agents, the tantalum metal of the present invention is completely inert and is not toxic to body tissue. The literature also discloses that powdered tantalum has been employed as a medium for bronchography (Invest. Radiol., Vol 3, 229–237, 1968). However, the only successful method of administration to the lungs prior to this invention has been by insufflation of the powder. There are many disadvantages associated with insufflation of powdered tantalum, the major disadvantage being that the powder is potentially flammable and may either burn or explode if the equipment being employed to administer the powder is not properly grounded in order to prevent sparks.

It is therefore the object of this invention to provide bronchographic X-ray contrast media compositions containing tantalum metal which can be conveniently and safely administered to the lungs in order to obtain sharp, clear X-ray films of the bronchial tree.

We have now discovered that when tantalum metal, not heretofore recognized as having utility in liquid bronchographic contrast media compositions, is incorporated in such liquid compositions having a critical viscosity and flow properties as hereinafter described and introduced into the bronchial tree of the lung, they allow X-ray films of surprisingly sharp clarity and detail to be made of the bronchial tree. In addition, tantalum metal is highly compatible with most common contrast media ingredients.

More specifically, in accordance with the present invention there are provided bronchographic contrast media compositions containing as the essential X-ray opaque ingredient a finely divided tantalum metal having an average particle diameter in the range from about 0.5 to 30 microns, and preferably in the range from about 1 to about 5 microns dispersed in a liquid vehicle.

Preferably the liquid vehicle will be an oily vehicle comprising fixed, bland vegetable oils or triglycerides. Exemplary of such oils would be, for example, almond oil, coconut oil, cottonseed oil, glyceryl trioleate, olive oil, palm oil, palm kernel oil, peanut oil, persic oil, safflower oil and sesame oil.

The finely divided tantalum powder is present in the contrast media compositions in a physiologically and pharmaceutically acceptable amount for use in obtaining X-ray films of sufficient clarity and detail for use in bronchography.

As used herein, the expression "physiologically and pharmaceutically acceptable amount" is intended to refer to that amount of X-ray opaque ingredient which when combined with common contrast media ingredients of a non-opaque nature (suspending agent, viscosity builder, surfactant, etc.) will give a smooth, flowable, evenly dispersed contrast media. Amounts greater than the aforementioned can yield a dispersion which is excessively viscous and difficult to flow into the bronchial tree of the lung. Lesser amounts than contemplated will fail to furnish the desired coating of the bronchial tree and will not allow the preparation of X-ray films of sufficient clarity and detail. This physiologically and pharmaceutically acceptable amount generally lies in the range from about 20% to about 70% by weight of the total contrast media and the preferred range is from about 30% to about 40% by weight of the contrast media.

While it is not completely understood why the tantalum metal possesses extremely high ability to produce clear and detailed bronchograms, it is believed that the explanation is as follows: The ability of the tantalum metal to block the passage of X-rays is related to the atomic structure of the metal itself. The ability of the tantalum metal to produce a clear and detailed bronchogram depends on coating the bronchial tree with the tantalum metal. According to our invention the contrast medium containing the tantalum metal is introduced into the upper part of the bronchial tree. The average sized patient is given approximately 15 to 20 mls. on each side within 15 to 20 seconds. The liquid contrast medium flows into the bronchi and bronchiols under the influence of gravity depositing a thin layer or coating of tantalum metal. The extent of coating depends among other factors on the viscosity of the contrast medium. If the viscosity is too high, flow of the contrast medium into the smaller bronchiols is inhibited. If the viscosity is too low, the contrast medium will flow into the pulmonary parenchyma resulting in a bronchogram of inferior quality because of alveola filling. The high ability of tantalum metal to adhere to the walls of the bronchial tree is probably related to the surface properties of the metal particles. It is also probable that the vehicle aids in the adherence of the metal particles.

The contrast media of the present invention may be prepared by addition of the finely divided tantalum metal to a liquid vehicle of an appropriate viscosity. The tantalum metal can be dispersed thoroughly throughout the vehicle by tumbling or agitation or any other solid dispersing technique generally known in the art.

An appropriate viscosity refers to a viscosity such that the medium flows readily into the bronchi and bronchiols of the lung without allowing significant flow into the pulmonary parenchyma. This appropriate viscosity generally lies in the range from about 100 centipoise to about 1,000 centipoise at body temperature (considered to be about 37° C.) and the preferred range is from about 500 centipoise to about 800 centipoise. This viscosity is intended to refer to an "apparent viscosity" as described in the art determined with a one point viscometer such as the Brookfield Viscometer.

It is also desirable but not necessary that the vehicle exhibit some degree of plastic or pseudoplastic flow with thixotropic properties. This behavior described in the art as non-Newtonian flow can be detected and measured with a variable shear rate viscometer such as the Rheomat 15 Viscometer. When measured on this type of viscometer the vehicle generally has a "plastic viscosity" in the range from about 50 centipoise to about 400 centipoise, preferably in the range from about 250 centipoise to about 350 centipoise and a "zero-shear rate viscosity" in the range from about 200 centipoise to about 600 centipoise, preferably in the range from about 350 centipoise to about 500 centipoise. A comprehensive definition of various viscosity terms can be found in chapter 1 of "Viscosity and Flow Measurement" published by Interscience, Inc., second printing, 1966. The actual value of the viscosity of the vehicle will depend considerably on the type of viscometer used to measure the viscosity.

The above desired viscosity may be obtained in the oily vehicle by the addition of a metallic soap which is oil soluble. These soaps are prepared from hydroxides of polyvalent metallic ions and fatty acids containing from about 12 to about 18 carbon atoms. Exemplary of the polyvalent metals are aluminum, calcium, or magnesium. The fatty acid may be, for example, lauric, palmitic, stearic, oleic, linoleic or myristic. Most advantageously an oily vehicle with suitable non-Newtonian flow properties can be prepared from peanut oil and a metallic soap such as aluminum stearate.

The amount of metallic soap generally lies in the range from about 5% to about 15% by weight of the total vehicle and the preferred range is from about 8% to about 12% by weight of the vehicle. The flow properties of this type of oily vehicle will depend to a greater or lesser extent on the method of preparation. The suggested method of preparation is as follows: The metallic soap is melted in the peanut oil at about 121° C. and stirred for a period of time, 15 minutes is usually sufficient to insure proper mixing and dispersion. The mixture is cooled to room temperature at a controlled rate while stirring, the preferred cooling rate is about 1° C. per 3 to 5 minutes.

Safety also requires that a bronchographic contrast media be sterile when introduced into the human lung. Any appropriate method of sterilization known in the art can be used. The following is an example which has been found to be effective and convenient. Aluminum stearate is melted in peanut oil at about 121° C. and stirred for about 15 minutes. The vehicle is placed in a dry air sterilizing oven at 160° C. for about 2 hours. The finely divided tantalum metal can also be sterilized by heating at 160° C. for about 2 hours in a dry air sterilizing oven. The sterile tantalum metal can be added aseptically to the sterile vehicle and dispersed thoroughly by tumbling. The mixture should be cooled to room temperature at a controlled rate, usually 1° C. per 3 to 5 minutes. The contrast media tends to be excessively viscous if cooled at a faster rate and excessively thin if cooled at a slower rate.

The amount of tantalum metal of the present invention which can be used in a bronchographic contrast media depends on the amount necessary for coating the bronchial tree of the lung without causing excessive thickening of the contrast media. It has been that because the tantalum metal tends to be more effective as an X-ray opaque agent than the iodine containing agents, a lesser amount of the tantalum metal need be incorporated into the contrast media.

Aqueous suspensions of finely divided tantalum metal are also intended to be included in the present invention. As thickening and suspending agents in aqueous suspensions there can be used gum tragacanth, sodium carboxymethylcellulose, hydroxyethylcellulose, carragheen and its derivatives, starch, acacia gums, agar agar and pectin. Those skilled in the contrast media art know other thickening and suspending agents. Methods of preparation and sterilization of aqueous suspension are also well known in the art.

The contrast media of the invention can also contain as optional ingredients a surfactant; dispersing agents, preservatives; buffers; and medicinal agents such as antibiotics and anesthetics in proportions to give any desired effect. These are conventional components of contrast media compositions, and materials suitable for this purpose need not be enumerated, for they are well known to those skilled in the contrast media art.

Medicinal agents are employed in a beneficial amount normally ranging from about 0.01% to about 5% by weight of the contrast media, the surfactants in an amount from about 0.01% to about 6% by weight of the contrast media, dispersing agents in an amount from about 0.01% to about 4% by weight of the contrast media, preservatives in an amount from about 0.01% to about 2% by weight of the contrast media, buffers in an amount from about 0.02% to about 10% by weight of the contrast media and suspending agents in an amount from about 0.5% to about 30% by weight of the contrast media.

EXAMPLE 1

| Ingredients: | Percent |
|---|---|
| Finely divided tantalum metal | 40.0 |
| Aluminum stearate | 5.4 |
| Peanut oil | 54.6 |
| Total | 100.0 |

EXAMPLE 2

| Ingredients: | Percent |
|---|---|
| Finely divided tantalum metal | 30.0 |
| Aluminum stearate | 6.0 |
| Dioctyl sodium sulfosuccinate | 0.7 |
| Peanut oil | 63.3 |
| Total | 100.0 |

EXAMPLE 3

| Ingredients: | Percent |
|---|---|
| Finely divided tantalum metal | 35.00 |
| Sodium carboxymethylcellulose | 1.30 |
| Sodium chloride | 0.58 |
| Methyl p-hydroxy benzoate | 0.06 |
| Water | 63.06 |
| Total | 100.0 |

EXAMPLE 4

| Ingredients: | Percent |
|---|---|
| Finely divided tantalum metal | 35.0 |
| Magnesium palmitate | 10.0 |
| Cottonseed oil | 55.0 |
| Total | 100.0 |

EXAMPLE 5

| Ingredients: | Percent |
|---|---|
| Finely divided tantalum metal | 50.0 |
| Calcium laurate | 8.0 |
| Sesame oil | 42.0 |
| Total | 100.0 |

It will be appreciated that various modifications and changes may be made in the contrast media compositions of the invention in addition to those enumerated above by those skilled in the contrast media art without departing from the essence of the invention, and accordingly, the invention is to be limited only within the scope of the appended claims.

We claim:

1. In the process of producing a bronchiograph using tantalum the improvement which comprises employing the tantalum in a composition comprising about 20 to about 70% by weight of finely divided tantalum metal having an average diameter of from about 0.5 to about 30 microns and from about 5% to about 15% of a metallic soap which is oil soluble and prepared from a hydroxide of a polyvalent metallic ion and a fatty acid containing from about 12 to about 18 carbon atoms, dispersed in a liquid vehicle which comprises the remainder of the composition said vehicle having an apparent viscosity of from about 100 centipoise to about 1,000 centipoise at body temperature as measured by a Brookfield Viscometer, and exhibiting non-Newtonian flow properties in an effective amount and administering said composition.

* * * * *

UNITED STATES PATENT OFFICE
CERTIFICATE OF CORRECTION

PATENT NO. : 3,937,800
DATED : February 10, 1976
INVENTOR(S) : Peter Dure-Smith and Roger L. Schnaare It is certified that error appears in the above-identified patent and that said Letters Patent are hereby corrected as shown below:

Front Page, after "Inventors", should read --
Peter Dure-Smith of Penn Valley, Pennsylvania, and
Roger L. Schnaare of Turnersville, New Jersey.

Column 6, Claim 1, lines 43 and 44, after "properties" should read --and administering said composition in an effective amount. --

Signed and Sealed this twentieth Day of April 1976

[SEAL]

Attest:

RUTH C. MASON
*Attesting Officer*

C. MARSHALL DANN
*Commissioner of Patents and Trademarks*